US010214608B2

(12) United States Patent
Minagawa

(10) Patent No.: US 10,214,608 B2
(45) Date of Patent: Feb. 26, 2019

(54) SURFACE MODIFICATION METHOD AND SURFACE-MODIFIED BODY

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

(*) Notice: Subject to any disclaimer, the term of this patent is extended or adjusted under 35 U.S.C. 154(b) by 0 days.

(21) Appl. No.: 15/201,874

(22) Filed: Jul. 5, 2016

(65) Prior Publication Data

US 2017/0037176 A1 Feb. 9, 2017

(30) Foreign Application Priority Data

Aug. 3, 2015 (JP) ................. 2015-153487

(51) Int. Cl.
*C08F 283/02* (2006.01)
*C08F 2/48* (2006.01)
*C08J 7/18* (2006.01)
*A61L 31/04* (2006.01)
*A61L 31/10* (2006.01)
*A61L 31/14* (2006.01)
*A61L 27/34* (2006.01)
*A61L 29/08* (2006.01)
*C08F 257/02* (2006.01)
*C08F 265/06* (2006.01)
*C08F 220/56* (2006.01)
*C08F 220/28* (2006.01)

(52) U.S. Cl.
CPC ............ *C08F 283/02* (2013.01); *A61L 27/34* (2013.01); *A61L 29/085* (2013.01); *A61L 31/049* (2013.01); *A61L 31/10* (2013.01); *A61L 31/14* (2013.01); *C08F 2/48* (2013.01); *C08F 257/02* (2013.01); *C08F 265/06* (2013.01); *C08J 7/18* (2013.01); *A61L 2400/18* (2013.01); *A61L 2420/02* (2013.01); *C08F 220/56* (2013.01); *C08F 2220/281* (2013.01)

(58) Field of Classification Search
CPC .................................................... C08F 283/08
See application file for complete search history.

(56) References Cited

U.S. PATENT DOCUMENTS

| | | |
|---|---|---|
| 3,418,066 A | 12/1968 | Caldwell et al. |
| 5,100,689 A | 3/1992 | Goldberg et al. |
| 5,154,727 A | 10/1992 | Dyer |
| 5,340,879 A | 8/1994 | Audenaert et al. |
| 5,453,467 A | 9/1995 | Bamford et al. |
| 5,637,460 A | 6/1997 | Swan et al. |
| 5,688,252 A | 11/1997 | Matsuda et al. |
| 5,855,623 A | 1/1999 | English et al. |
| 5,885,566 A | 3/1999 | Goldberg |
| 5,889,073 A | 3/1999 | Zhang et al. |
| 5,967,714 A | 10/1999 | Ottersbach et al. |
| 6,001,894 A | 12/1999 | Ottersbach et al. |
| 6,188,075 B1 | 2/2001 | Takayama et al. |
| 6,203,856 B1 | 3/2001 | Ottersbach et al. |
| 6,228,172 B1 | 5/2001 | Taylor et al. |
| 6,358,557 B1* | 3/2002 | Wang ............... A61L 29/085 427/2.24 |
| 6,808,738 B2 | 10/2004 | Ditizio et al. |
| 7,348,055 B2 | 3/2008 | Chappa et al. |
| 8,299,139 B1 | 10/2012 | Taranekar et al. |
| 8,323,750 B2* | 12/2012 | Yang ............... C07D 311/86 210/500.21 |
| 8,840,927 B2 | 9/2014 | Ditizio et al. |
| 9,339,845 B2 | 5/2016 | Minagawa |
| 9,469,738 B1 | 10/2016 | Minagawa |

(Continued)

FOREIGN PATENT DOCUMENTS

| | | |
|---|---|---|
| CN | 101372538 A | 2/2009 |
| CN | 101565489 A | 10/2009 |

(Continued)

OTHER PUBLICATIONS

PLaczek et al. Photosensitizing Properties of Compounds Related to Benzophenone. Acto Dermato Vernereologica, 2013, 93; pp. 30-32 (Year: 2013).*
International Search Report and English translation thereof, dated Jan. 21, 2014, for International Application No. PCT/JP2013/081090.
Jinan Haohua Industry Co., Ltd., "Ethanaminum, N,N,N-trimethyl-2-[(2-methyl-1-oxo-2-propen-1-yl) oxy]-, chloride (1:1)," CAS: 5039-78-1, Product Information Inquiry Description, found online on Dec. 27, 2016, pp. 1-2 (3 pages), http://guide7932.guidechem.com/pro-show2436647.html.

(Continued)

*Primary Examiner* — Sanza L. McClendon
(74) *Attorney, Agent, or Firm* — Birch, Stewart, Kolasch & Birch LLP

(57) ABSTRACT

Methods are provided for surface-modifying a rubber vulcanizate or a thermoplastic resin. The methods allow these objects to have a chemically fixed surface layer that exhibits not only low adsorption or selective adsorption properties with respect to proteins and cells, but also excellent durability, instead of having a coating which has drawbacks such as reduction in properties due to separation or peeling of the coating. Included is a method for surface-modifying an object made of a rubber vulcanizate or a thermoplastic resin, the method including: a step 1 of forming polymerization initiation points on the surface of the object; and a step 2 of radically polymerizing a hydrophilic monomer starting from the polymerization initiation points by irradiation with UV light having a wavelength of 300 to 400 nm in the presence of an alkali metal salt to grow polymer chains on the surface of the object.

24 Claims, No Drawings

(56) References Cited

U.S. PATENT DOCUMENTS

| | | |
|---|---|---|
| 9,758,605 B2 | 9/2017 | Minagawa |
| 9,982,105 B2 | 5/2018 | Minagawa |
| 2002/0161065 A1 | 10/2002 | Ditizio et al. |
| 2004/0086568 A1 | 5/2004 | Ditizio et al. |
| 2004/0106732 A1 | 6/2004 | Tsuji et al. |
| 2005/0137355 A1 | 6/2005 | Buckanin et al. |
| 2005/0168685 A1 | 8/2005 | Katagiri et al. |
| 2006/0155057 A1 | 7/2006 | Hermeling et al. |
| 2007/0003592 A1 | 1/2007 | Hissink |
| 2007/0116971 A1 | 5/2007 | Yoshikawa et al. |
| 2008/0016644 A1 | 1/2008 | Mizote et al. |
| 2008/0103287 A1 | 5/2008 | Chino et al. |
| 2008/0312377 A1 | 12/2008 | Schmidt et al. |
| 2009/0169715 A1 | 7/2009 | Dias et al. |
| 2009/0239089 A1 | 9/2009 | Agata et al. |
| 2009/0257022 A1 | 10/2009 | Abe et al. |
| 2010/0053547 A1 | 3/2010 | Baude et al. |
| 2010/0255336 A1 | 10/2010 | Zabinski |
| 2011/0124766 A1 | 5/2011 | Yang et al. |
| 2011/0160357 A1 | 6/2011 | Gerster et al. |
| 2011/0274940 A1 | 11/2011 | Kyomoto et al. |
| 2012/0021151 A1 | 1/2012 | Tatarka et al. |
| 2012/0100369 A1 | 4/2012 | Hanazawa et al. |
| 2013/0203883 A1 | 8/2013 | Minagawa |
| 2013/0274367 A1 | 10/2013 | Minagawa et al. |
| 2013/0310772 A1 | 11/2013 | Minagawa |
| 2014/0039084 A1 | 2/2014 | Minagawa |
| 2014/0128493 A1 | 5/2014 | Minagawa |
| 2015/0203612 A1 | 7/2015 | Minagawa |

FOREIGN PATENT DOCUMENTS

| | | |
|---|---|---|
| CN | 102382291 A | 3/2012 |
| CN | 202427397 U | 9/2012 |
| CN | 103242553 A | 8/2013 |
| CN | 104119552 A | 10/2014 |
| EP | 0 872 512 A2 | 10/1998 |
| EP | 2 623 335 A2 | 8/2013 |
| EP | 2 664 627 A1 | 11/2013 |
| EP | 2 796 155 A1 | 10/2014 |
| EP | 2 894 191 A1 | 7/2015 |
| GB | 1120803 A | 7/1968 |
| GB | 1120804 A | 7/1968 |
| JP | 60-221410 A | 11/1985 |
| JP | 61-209667 A | 9/1986 |
| JP | 62-87163 A | 4/1987 |
| JP | 63-92658 A | 4/1988 |
| JP | 5-43634 A | 2/1993 |
| JP | 5-76590 A | 3/1993 |
| JP | 5-179055 A | 7/1993 |
| JP | 6-25450 A | 2/1994 |
| JP | 6-510322 A | 11/1994 |
| JP | 7-100744 B2 | 11/1995 |
| JP | 8-1793 A | 1/1996 |
| JP | 9-31361 A | 2/1997 |
| JP | 9-67457 A | 3/1997 |
| JP | 9-108359 A | 4/1997 |
| JP | 9-313594 A | 12/1997 |
| JP | 10-90500 A | 4/1998 |
| JP | 10-251350 A | 9/1998 |
| JP | 10-298320 A | 11/1998 |
| JP | 11-192305 A | 7/1999 |
| JP | 2000-273229 A | 10/2000 |
| JP | 2001-31871 A | 2/2001 |
| JP | 2001-46956 A | 2/2001 |
| JP | 2001-95621 A | 4/2001 |
| JP | 2002-145971 A | 5/2002 |
| JP | 2002-544346 A | 12/2002 |
| JP | 2003-2903 A | 1/2003 |
| JP | 2003-510378 A | 3/2003 |
| JP | 2004-528418 A | 9/2004 |
| JP | 2004-298220 A | 10/2004 |
| JP | 2005-3817 A | 1/2005 |
| JP | 2005-516736 A | 6/2005 |
| JP | 2005-208290 A | 8/2005 |
| JP | 2005-213516 A | 8/2005 |
| JP | 2005-523981 A | 8/2005 |
| JP | 2005-253538 A | 9/2005 |
| JP | 2007-77286 A | 3/2007 |
| JP | 2007-119563 A | 5/2007 |
| JP | 2007-145884 A | 6/2007 |
| JP | 2007-514861 A | 6/2007 |
| JP | 2007-202965 A | 8/2007 |
| JP | 2008-73883 A | 4/2008 |
| JP | 2009-30074 A | 2/2009 |
| JP | 2009-518479 A | 5/2009 |
| JP | 2009-138169 A | 6/2009 |
| JP | 2009-226718 A | 10/2009 |
| JP | 2009-227842 A | 10/2009 |
| JP | 2010-23710 A | 2/2010 |
| JP | 2010-508541 A | 3/2010 |
| JP | 2010-142537 A | 7/2010 |
| JP | 2010-142573 A | 7/2010 |
| JP | 2010-150349 A | 7/2010 |
| JP | 4523532 B2 | 8/2010 |
| JP | 2010-216964 A | 9/2010 |
| JP | 2010-229180 A | 10/2010 |
| JP | 2011-42755 A | 3/2011 |
| JP | 2011-67362 A | 4/2011 |
| JP | 2011-188908 A | 9/2011 |
| JP | 2011-189562 A | 9/2011 |
| JP | 2011-208133 A | 10/2011 |
| JP | 2011-219520 A | 11/2011 |
| JP | 2011-241190 A | 12/2011 |
| JP | 2012-105579 A | 6/2012 |
| JP | WO 2012/091169 A1 | 7/2012 |
| JP | 2012-162646 A | 8/2012 |
| JP | 2013-159629 A | 8/2013 |
| JP | 2013-159667 A | 8/2013 |
| JP | 2013-208777 A | 10/2013 |
| JP | 2013-237801 A | 11/2013 |
| JP | 2013-237802 A | 11/2013 |
| JP | 2014-31429 A | 2/2014 |
| JP | 2014-31430 A | 2/2014 |
| JP | 2014-108153 A | 6/2014 |
| WO | WO 93/05081 A1 | 3/1993 |
| WO | WO 03/068289 A1 | 8/2003 |
| WO | WO 03/093357 A1 | 11/2003 |
| WO | WO 2007/065721 A2 | 6/2007 |
| WO | WO 2007/072613 A1 | 6/2007 |
| WO | WO 2008/053712 A1 | 5/2008 |
| WO | WO 2010/058848 A1 | 5/2010 |
| WO | WO 2010/131652 A1 | 11/2010 |
| WO | WO 2011/038483 A1 | 4/2011 |
| WO | WO 2012/165525 A1 | 12/2012 |

OTHER PUBLICATIONS

Allmér et al., "Surface Modification of Polymers. I. Vapour Phase Photografting with Acrylic Acid," Journal of Polymer Science: Part A: Polymer Chemistry, vol. 26, 1988, pp. 2099-2111.

International Search Report issued in PCT/JP2013/074219 dated Dec. 3, 2013.

International Search Report, dated Jul. 24, 2012, for International Application No. PCT/JP2012/064030.

U.S. Non-Final Office Action, dated May 8, 2015, for U.S. Appl. No. 13/756,837.

U.S. Non-Final Office Action, dated Oct. 20, 2014, for U.S. Appl. No. 13/756,837.

U.S. Notice of Allowance, dated Dec. 26, 2014, for U.S. Appl. No. 13/956,974.

U.S. Office Action (Requirement for Restriction/Election), dated May 9, 2014, for U.S. Appl. No. 13/956,974.

U.S. Office Action dated Jun. 24, 2015, for U.S. Appl. No. 14/118,136.

U.S. Office Action dated Sep. 21, 2015, for U.S. Appl. No. 14/107,746.

U.S. Office Action, dated Apr. 17, 2015, for U.S. Appl. No. 13/775,451.

U.S. Office Action, dated Aug. 25, 2014, for U.S. Appl. No. 13/956,974.

International Search Report and Written Opinion of the International Searching Authority, issued in PCT/JP2014/079947, dated Jan. 20, 2015.

(56) References Cited

OTHER PUBLICATIONS

International Search Report, dated Feb. 25, 2014, for International Application No. PCT/JP2013/082409.
International Search Report, issued in PCT/JP2014/063268, dated Aug. 19, 2014.
U.S. Office Action, dated Nov. 3, 2016, for U.S. Appl. No. 14/896,096.
"Fundamental of Polymer Chemistry and Physics," edited by Wuji Wei and etc., Chemical Industry Press, Oct. 2011, pp. 59-60 (4 pages total).
English translation of the Chinese Office Action, dated Sep. 22, 2017, for Chinese Application No. 201380044153.X.
English translation of the Chinese Office Action for Chinese Application No. 201480032195.6, dated Jan. 24, 2018.
International Search Report (Form PCT/ISA/210) for International Application No. PCT/JP2014/082367, dated Mar. 3, 2015, with an English translation.
Written Opinion of the International Searching Authority (Form PCT/ISA/237) for International Application No. PCT/JP2014/082367, dated Mar. 3, 2015, with an English translation.
Zhang et al., "Corona Radiation Technology" China Textile Press, May 2003, p. 14 (3 pages total).
International Search Report and English translation for Application No. PCT/JP2015/070547 (PCT/ISA/210) dated Oct. 6, 2015.
Written Opinion of the International Searching Authority and English translation for Application No. PCT/JP2015/070547 (PCT/ISA/237) dated Oct. 6, 2015.

\* cited by examiner

SURFACE MODIFICATION METHOD AND SURFACE-MODIFIED BODY

TECHNICAL FIELD

The present invention relates to methods for surface modification which provide surfaces with low adhesion properties with respect to proteins and cells in blood or biological fluids or selective adhesion properties with respect to cancer cells or other cells. The present invention also relates to surface-modified bodies of, for example, matrices, filters, channels, and tubes for medical and healthcare use, at least part of whose surface is modified by the methods.

BACKGROUND ART

Matrices, filters, channels, tubes, and other devices for medical and healthcare use or other uses have a drawback in that since they come into contact with blood or biological fluids inside or outside the body during use, proteins and cells in the blood or biological fluids adhere or adsorb to the surface of the devices and thereby impair the original function of the devices. It is also desired that these devices selectively adsorb and collect specific cells such as cancer cells for capture and use in diagnosis or treatment. However, unfortunately, it is difficult to selectively adsorb the specific cells.

Patent Literatures 1 and 2 propose to coat the surface of matrices, filters, channels, or tubes for medical and healthcare use with a polymer of a hydrophilic monomer to solve the problems mentioned above. However, these methods have a durability problem in that the coating layer is separated or peeled due to the hydrophilicity.

CITATION LIST

Patent Literature

Patent Literature 1: JP 2005-516736 T
Patent Literature 2: JP 2005-523981 T

SUMMARY OF INVENTION

Technical Problem

The present invention aims to solve the aforementioned problems and provide methods for surface-modifying a rubber vulcanizate or a thermoplastic resin. The methods allow these objects to have a chemically fixed surface layer that exhibits not only low adsorption or selective adsorption properties with respect to proteins and cells, but also excellent durability, instead of having a coating which has drawbacks such as reduction in properties due to separation or peeling of the coating. The present invention also aims to provide surface-modified bodies of, for example, matrices, filters, channels, and tubes for medical and healthcare use, at least part of whose surface is modified by the methods.

Solution to Problem

The present invention relates to a method for surface-modifying an object made of a rubber vulcanizate or a thermoplastic resin, the method including: a step 1 of forming polymerization initiation points on a surface of the object; and a step 2 of radically polymerizing a hydrophilic monomer starting from the polymerization initiation points by irradiation with UV light having a wavelength of 300 to 400 nm in the presence of an alkali metal salt to grow polymer chains on the surface of the object.

The present invention relates to a method for surface-modifying an object made of a rubber vulcanizate or a thermoplastic resin, the method including a step I of radically polymerizing a hydrophilic monomer by irradiation with UV light having a wavelength of 300 to 400 nm in the presence of a photopolymerization initiator and an alkali metal salt to grow polymer chains on a surface of the object.

The step 1 preferably includes adsorbing a photopolymerization initiator to a surface of the object, optionally followed by irradiation with UV light having a wavelength of 300 to 400 nm, to form polymerization initiation points from the photopolymerization initiator on the surface.

Before the step 1 or step I, the method preferably includes a step of making the surface of the object hydrophilic by irradiation with light having a wavelength of 160 to 300 nm.

The photopolymerization initiator is preferably at least one of a benzophenone compound or a thioxanthone compound.

The alkali metal salt is preferably at least one of sodium chloride or potassium chloride.

It is preferred that during or before the light irradiation, an inert gas is introduced into a reaction vessel, a reaction pipe, and a reaction solution so that the monomer is polymerized in an atmosphere replaced with the inert gas.

The radical polymerization of the hydrophilic monomer in the step 2 or step I is preferably carried out by applying or spraying a solution of the hydrophilic monomer onto the surface of the object, and then covering the applied or sprayed object with a transparent cover of glass or resin, followed by irradiation with the UV light through the transparent cover of glass or resin to radically polymerize the monomer.

The hydrophilic monomer is preferably at least one selected from the group consisting of acrylic acid, acrylic acid esters, alkali metal salts of acrylic acid, amine salts of acrylic acid, methacrylic acid, methacrylic acid esters, alkali metal salts of methacrylic acid, amine salts of methacrylic acid, acrylonitrile, acrylamide, dimethylacrylamide, diethylacrylamide, isopropylacrylamide, hydroxyethylacrylamide, methoxyethylacrylamide, acryloylmorpholine, methacrylamide, dimethylmethacrylamide, diethylmethacrylamide, isopropylmethacrylamide, hydroxyethylmethacrylamide, methoxyethylmethacrylamide, and methacryloylmorpholine.

The hydrophilic monomer is preferably an alkali metal salt-containing monomer.

The alkali metal salt-containing monomer is preferably at least one selected from the group consisting of alkali metal salts of acrylic acid, methacrylic acid, itaconic acid, 3-vinylpropionic acid, vinylsulfonic acid, 2-sulfoethyl (meth)acrylate, 3-sulfopropyl (meth)acrylate, 2-acrylamide-2-methylpropanesulfonic acid, or styrenesulfonic acid.

The hydrophilic monomer is preferably a halogen-containing monomer.

The halogen-containing monomer is preferably a nitrogen-containing monomer.

The nitrogen-containing monomer is preferably at least one of 2-(methacryloyloxy)ethyl trimethylammonium chloride or 2-(acryloyloxy)ethyl trimethylammonium chloride.

The hydrophilic monomer is preferably a zwitterionic monomer.

Preferably, the solution of the hydrophilic monomer contains a polymerization inhibitor, and the monomer is polymerized in the presence of the polymerization inhibitor.

The present invention relates to a surface-modified body, produced by any of the methods.

The present invention relates to a surface-modified body, produced by any of the methods, to which proteins and cells in blood or biological fluids are less likely to adhere or adsorb.

The present invention relates to a surface-modified body, produced by any of the methods, to which a specific protein or specific cells in blood or biological fluids are more likely to selectively adhere or adsorb.

The present invention relates to a surface-modified body, including a three-dimensional solid body at least part of whose surface is modified by any of the methods.

The present invention relates to a matrix for medical and healthcare use, at least part of whose surface is modified by any of the methods.

The present invention relates to a filter for medical and healthcare use, at least part of whose surface is modified by any of the methods.

The present invention relates to a channel for medical and healthcare use, at least part of whose surface is modified by any of the methods.

The present invention also relates to a tube for medical and healthcare use, at least part of whose surface is modified by any of the methods.

Advantageous Effects of Invention

The methods for surface-modifying an object made of a rubber vulcanizate or a thermoplastic resin of the present invention include a step 1 of forming polymerization initiation points on the surface of the object, and a step 2 of radically polymerizing a hydrophilic monomer starting from the polymerization initiation points by irradiation with UV light having a wavelength of 300 to 400 nm in the presence of an alkali metal salt to grow polymer chains on the surface of the object; or include a step I of radically polymerizing a hydrophilic monomer by irradiation with UV light having a wavelength of 300 to 400 nm in the presence of a photopolymerization initiator and an alkali metal salt to grow polymer chains on the surface of the object. Such methods allow the objects to have a surface with a hydrophilic polymer fixed thereon, and thus provide them with not only low adsorption properties with respect to proteins and cells or selective adsorption properties with respect to a specific protein or specific cells, but also durability after repeated use, thereby sufficiently suppressing deterioration of the low adhesion properties or selective adhesion properties. Thus, by forming hydrophilic polymer chains on the surface of objects using the methods, it is possible to produce surface-modified bodies of, for example, matrices, filters, channels, and tubes for medical and healthcare use, which are excellent in the above properties.

DESCRIPTION OF EMBODIMENTS

One aspect of the present invention is a method for surface-modifying an object made of a rubber vulcanizate or a thermoplastic resin, which includes: a step 1 of forming polymerization initiation points on the surface of the object; and a step 2 of radically polymerizing a hydrophilic monomer starting from the polymerization initiation points by irradiation with UV light having a wavelength of 300 to 400 nm in the presence of an alkali metal salt to grow polymer chains on the surface of the object.

Before the step 1, the method of the present invention may suitably include a step of making the surface of the object hydrophilic by irradiation with light having a wavelength of 160 to 300 nm. When the surface of the object is made hydrophilic by irradiation with the light before the step 1 of adsorbing a photopolymerization initiator to the surface of the object, the surface has better compatibility with an organic solvent containing the photopolymerization initiator dissolved therein, with the result that a greater amount of the photopolymerization initiator is more uniformly adsorbed on the surface of the object in the step 1. The irradiation with light having a wavelength of 160 to 300 nm may be carried out by conventionally known methods, such as using low-pressure mercury lamps, Xe excimer lamps, or high-pressure mercury lamps. Among these, low-pressure mercury lamps are preferred because they can highly efficiently make the surface hydrophilic.

Polymerization initiation points are formed on the surface of a formed rubber vulcanizate or a formed thermoplastic resin (an object to be modified) in the step 1 after the surface of the object is optionally made hydrophilic by the above step. For example, the step 1 may be carried out, for example, by adsorbing a photopolymerization initiator to the surface of the object to form polymerization initiation points, or by adsorbing a photopolymerization initiator to the surface of the object and then irradiating the surface with UV light having a wavelength of 300 to 400 nm to form polymerization initiation points from the photopolymerization initiator on the surface.

Examples of thermoplastic resins that can be used as the object to be modified include polyethylene terephthalate (PET), polystyrene, polycarbonate, polytetrafluoroethylene, and polydimethylsiloxane.

Examples of rubber vulcanizates that can be used as the object to be modified include silicone rubber, fluororubber, natural rubber, deproteinized natural rubber, styrene-butadiene rubber, polybutadiene rubber, polyisoprene rubber, and butyl rubber and halogenated butyl rubber which have a degree of unsaturation of a few percent of isoprene units.

The conditions for vulcanization of the rubber may be selected appropriately, and the vulcanization temperature of the rubber is preferably 140° C. or higher, more preferably 170° C. or higher, and still more preferably 175° C. or higher.

Examples of the photopolymerization initiator include carbonyl compounds, organic sulfur compounds such as tetraethylthiuram disulfide, persulfides, redox compounds, azo compounds, diazo compounds, halogen compounds, and photoreducing dyes. Preferred among these are carbonyl compounds.

Preferred among carbonyl compounds serving as photopolymerization initiators are benzophenone and derivatives thereof (benzophenone compounds). For example, suitable are benzophenone compounds represented by the following formula:

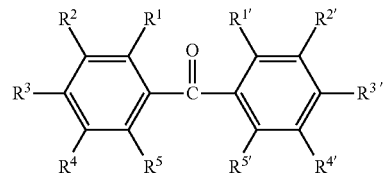

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxy group, a primary to tertiary amino group, a mercapto group, or a hydrocarbon group optionally containing an oxygen, nitrogen, or sulfur atom, and any two adjacent groups of $R^1$ to $R^5$ and $R^{1'}$ to $R^{5'}$ may be joined together to form a ring with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone because they contribute to forming polymer brushes well.

The photopolymerization initiator may also suitably be a thioxanthone compound because it provides a high polymerization rate and is easily adsorbed to and/or reacted with rubber or the like. For example, suitable are compounds represented by the following formula:

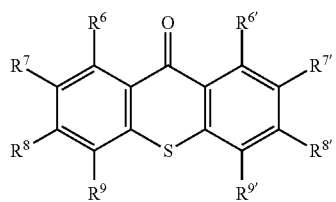

wherein $R^6$ to $R^9$ and $R^{6'}$ to $R^{9'}$ are the same as or different from one another and each represent a hydrogen atom, a halogen atom, or an alkyl, cyclic alkyl, aryl, alkenyl, alkoxy, or aryloxy group.

Examples of thioxanthone compounds represented by the above formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are those which are substituted at one or two, especially two, of $R^6$ to $R^9$ and $R^{6'}$ to $R^{9'}$ with alkyl groups. More preferred is 2,4-diethylthioxanthone.

The adsorbing of the photopolymerization initiator such as a benzophenone or thioxanthone compound to the surface of the object may be carried out as follows. In the case of a benzophenone or thioxanthone compound, for example, the benzophenone or thioxanthone compound is dissolved in an organic solvent to prepare a solution; a surface portion of the object to be modified is treated with this solution so that the compound is adsorbed on the surface; and, if necessary, the organic solvent is dried and evaporated, whereby polymerization initiation points are formed. The surface-treating method may be any method that allows the solution of the benzophenone or thioxanthone compound to be brought into contact with the surface of the object. Suitable methods include application or spraying of the benzophenone or thioxanthone compound solution; or immersion into the solution. Moreover, if only part of the surface needs to be modified, it is sufficient to adsorb the photopolymerization initiator only to the necessary part of the surface. In this case, for example, application or spraying of the solution is suitable. Examples of the solvent include methanol, ethanol, acetone, benzene, toluene, methyl ethyl ketone, ethyl acetate, and THF. Acetone is preferred because it does not swell the object intended to be modified, and it dries and evaporates quickly.

As described, after the photopolymerization initiator is adsorbed on the surface of the object, the surface may then be irradiated with UV light having a wavelength of 300 to 400 nm to form polymerization initiation points from the photopolymerization initiator on the surface. This UV irradiation may be carried out by known methods, for example, as described for the UV irradiation in the step 2, which will be described below.

In the step 2, a hydrophilic monomer is radically polymerized starting from the polymerization initiation points formed in the step 1, by irradiation with UV light having a wavelength of 300 to 400 nm in the presence of an alkali metal salt to grow polymer chains on the surface of the object. In particular, by carrying out the step 2 in the presence of an alkali metal salt, the hydrophilic polymer is sufficiently fixed to the surface of the object, and therefore the object has excellent low adsorption properties with respect to proteins and cells or excellent selective adsorption properties with respect to a specific protein or specific cells, and further has improved durability after repeated use so that deterioration of the low adhesion properties or selective adhesion properties is suppressed.

Examples of alkali metal salts that can be used include halogenated alkali metal salts, alkali metal carbonates, alkali metal bicarbonates, alkali metal hydrogen carbonates, alkali metal nitrates, alkali metal sulfates, alkali metal bisulfates, alkali metal phosphates, alkali metal hydroxides, alkali metal acetates, alkali metal citrates, and alkali metal lactates. The alkali metal salt may be a water-soluble lithium, sodium, potassium, rubidium, or cesium salt.

Specific examples include sodium chloride, potassium chloride, cesium chloride, sodium bromide, potassium bromide, sodium nitrate, potassium nitrate, sodium carbonate, potassium carbonate, sodium sulfate, potassium sulfate, sodium bisulfate, potassium bisulfate (potassium hydrogensulfate), sodium phosphate, potassium phosphate, sodium hydroxide, potassium hydroxide, sodium hydrogen carbonate, sodium dihydrogen phosphate, disodium hydrogen phosphate, trisodium phosphate, sodium acetate, potassium acetate, sodium citrate, potassium citrate, sodium lactate, and potassium lactate. The alkali metal salts may be used alone or in combinations of two or more.

In view of low adhesion properties, selective adhesion properties, and durability after repeated use, halogenated alkali metal salts are preferred among these, with sodium chloride or potassium chloride being particularly preferred.

The hydrophilic monomer may be a monomer containing a functional group that can be converted to a hydrophilic functional group, and examples include monomers containing hydrophilic groups, such as typically an amide group, a sulfuric acid group, a sulfonic acid group, a carboxylic acid group, a hydroxy group, an amino group, an oxyethylene group, or precursor functional groups of these groups. The hydrophilic monomers may be used alone or in combinations of two or more.

Specific examples of the hydrophilic monomer include (meth)acrylic acid, (meth)acrylic acid esters such as methoxyethyl (meth)acrylate and hydroxyethyl (meth)acrylate, alkali metal salts of (meth)acrylic acid, and amine salts of (meth)acrylic acid. Monomers containing a C—N bond in the molecule may also be mentioned. Examples of the monomer containing a C—N bond in the molecule include (meth)acrylamide; N-alkyl-substituted (meth)acrylamide derivatives such as N-ethyl(meth)acrylamide, N-n-propyl (meth)acrylamide, N-isopropyl(meth)acrylamide, N-cyclopropyl(meth)acrylamide, N-methoxyethyl(meth)acrylamide, and N-ethoxyethyl(meth)acrylamide; N,N-dialkyl-substituted (meth)acrylamide derivatives such as N,N-dimethyl(meth)acrylamide, N,N-ethylmethyl(meth)acrylamide, and N,N-diethyl(meth)acrylamide; hydroxy(meth)acrylamide; hydroxy(meth)acrylamide derivatives such as N-hydroxyethyl(meth)acrylamide; and cyclic group-containing (meth)acrylamide derivatives such as (meth)acryloylmorpholine. Preferred among these are (meth)acrylic acid, (meth)acrylic acid esters, alkali metal salts of (meth)acrylic acid, amine salts of (meth)acrylic acid, acrylonitrile, (meth)acrylamide, dimethyl(meth)acrylamide, diethyl(meth)acrylamide, isopropyl(meth)acrylamide, hydroxyethyl(meth)acrylamide, methoxyethyl(meth)acrylamide, and (meth)acryloylmorpholine. More preferred is (meth)acrylamide or 2-methoxyethyl acrylate, with 2-methoxyethyl acrylate being particularly preferred.

Suitable examples of the hydrophilic monomer also include alkali metal salt-containing monomers (monomers each containing an alkali metal in the molecule), zwitterionic monomers (zwitterionic group-containing compounds: compounds each bearing a center of permanent positive charge and a center of negative charge), and halogen-containing monomers (monomers each containing a halogen in the molecule). These monomers may be used alone or in combinations of two or more. If hydrophilic monomers simultaneously correspond to two or more of the above types of monomers, i.e. alkali metal salt-containing monomers, zwitterionic monomers, and halogen-containing monomers, as in the case of, for example, a hydrophilic monomer containing an alkali metal and a halogen (corresponding to both the alkali metal salt-containing monomer type and the halogen-containing monomer type), they are included in any of the two or more monomer types. The monomers may be used alone or in combinations of two or more.

Examples of the alkali metal salt-containing monomer include alkali metal salts of acrylic acid such as sodium acrylate and potassium acrylate; alkali metal salts of methacrylic acid such as sodium methacrylate and potassium methacrylate; alkali metal salts of itaconic acid such as sodium itaconate and potassium itaconate; alkali metal salts of 3-vinylpropionic acid such as sodium 3-vinylpropionate and potassium 3-vinylpropionate; alkali metal salts of vinylsulfonic acid such as sodium vinylsulfonate and potassium vinylsulfonate; alkali metal salts of 2-sulfoethyl (meth)acrylate such as sodium 2-sulfoethyl (meth)acrylate and potassium 2-sulfoethyl (meth)acrylate; alkali metal salts of 3-sulfopropyl (meth)acrylate such as sodium 3-sulfopropyl (meth)acrylate and potassium 3-sulfopropyl (meth)acrylate; alkali metal salts of 2-acrylamide-2-methylpropanesulfonic acid such as sodium 2-acrylamide-2-methylpropanesulfonate and potassium 2-acrylamide-2-methylpropanesulfonate; and alkali metal salts of styrenesulfonic acid such as sodium styrenesulfonate and potassium styrenesulfonate. Preferred among these is potassium 3-sulfopropyl methacrylate.

Examples of the zwitterionic monomer include carboxybetaines, sulfobetaines, and phosphobetaines. Other examples include compounds represented by the formula (1) below. Suitable among these compounds are compounds represented by the formula (2) below.

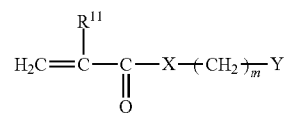
(1)

In the formula, $R^{11}$ represents —H or —CH$_3$; X represents —O—, —NH— or —N$^+$—; m represents an integer of 1 or greater; and Y represents a zwitterionic group or a halogen group such as Cl$^-$, Br$^-$, or F$^-$.

In the formula (1), it is preferred that $R^{11}$ is —CH$_3$, X is —O—, and m is an integer of 1 to 10. In the zwitterionic group designated by Y, the cation may be a quaternary ammonium such as tetraalkylammonium, and the anion may be a carboxylate, sulfonate, or phosphate.

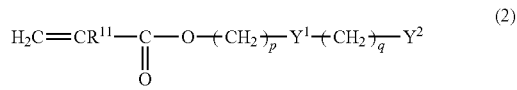
(2)

In the formula, $R^{11}$ represents —H or —CH$_3$; p and q each represent an integer of 1 or greater; and $Y^1$ and $Y^2$ represent ionic functional groups having electric charges opposite to each other.

In the formula (2), p is preferably an integer of 2 or greater, more preferably an integer of 2 to 10; and q is preferably an integer of 1 to 10, more preferably an integer of 2 to 4. Preferred $R^{11}$ groups are as identified above. $Y^1$ and $Y^2$ are as described for the cation and anion above.

Typical suitable examples of the zwitterionic monomer include compounds represented by the following formulas (2-1) to (2-4):

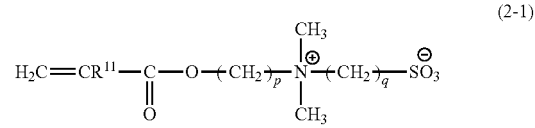
(2-1)

wherein $R^{11}$ represents a hydrogen atom or a methyl group, and p and q each represent an integer of 1 to 10;

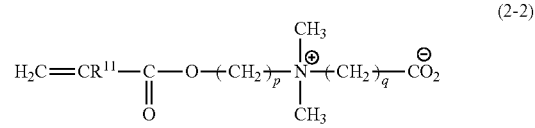
(2-2)

wherein $R^{11}$ represents a hydrogen atom or a methyl group, and p and q each represent an integer of 1 to 10;

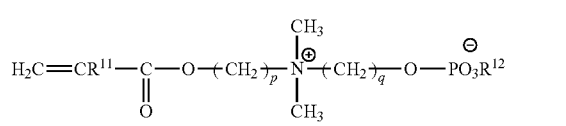
(2-3)

wherein $R^{11}$ represents a hydrogen atom or a methyl group, $R^{12}$ represents a C1-C6 hydrocarbon group, and p and q each represent an integer of 1 to 10; and

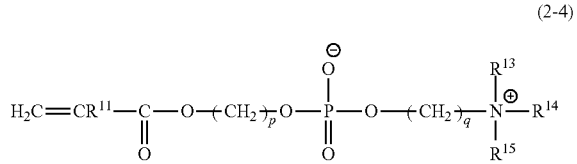

(2-4)

wherein $R^{11}$ represents a hydrogen atom or a methyl group, $R^{13}$, $R^{14}$, and $R^{15}$ are the same as or different from one another and each represent a C1-C2 hydrocarbon group, and p and q each represent an integer of 1 to 10.

Examples of compounds represented by the formula (2-1) include dimethyl(3-sulfopropyl) (2-(meth)acryloyloxyethyl)-ammonium betaine. Examples of compounds represented by the formula (2-2) include dimethyl(2-carboxyethyl)-(2-(meth)acryloyloxyethyl)ammonium betaine. Examples of compounds represented by the formula (2-3) include dimethyl(3-methoxyphosphopropyl) (2-(meth)acryloyloxyethyl)-ammonium betaine. Examples of compounds represented by the formula (2-4) include 2-(meth)acryloyloxyethyl phosphorylcholine. Other zwitterionic monomers include 2-(meth)acryloyloxyethyl carboxybetaine and 2-(meth)acryloyloxyethyl sulfobetaine. Preferred among these is 2-(meth)acryloyloxyethyl phosphorylcholine because of its high biocompatibility, i.e. low protein adsorbability.

The halogen-containing monomer refers to a hydrophilic monomer containing a halogen atom in the molecule. The halogen-containing monomers may be used alone or in combinations of two or more.

In view of low adhesion properties, selective adhesion properties, and durability after repeated use, the halogen-containing monomer may suitably be a nitrogen-containing monomer (halogen- and nitrogen-containing monomer). Specific preferred examples of such monomers include compounds represented by the following formula (I):

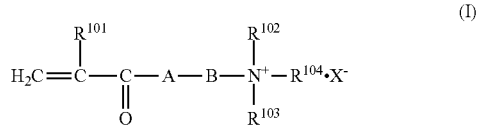

(I)

wherein A represents an oxygen atom or NH; B represents a C1-C4 alkylene group; $R^{101}$ represents a hydrogen atom or a methyl group; $R^{102}$, $R^{103}$, and $R^{104}$ are the same or different from one another and each represent a C1-C4 alkyl group; and $X^-$ represents a halogen ion.

The symbol A is preferably an oxygen atom. The symbol B may be a linear or branched alkylene group such as a methylene group, an ethylene group, or a propylene group, with a methylene group or an ethylene group being preferred. Each of $R^{102}$ to $R^{104}$ may be a linear or branched alkyl group such as a methyl group, an ethyl group, or a propyl group, with a methyl group or an ethyl group being preferred. The symbol X (halogen atom) may be, for example, fluorine, chlorine, or bromine, preferably chlorine.

Examples of nitrogen-containing monomers represented by the formula (I) include 2-(methacryloyloxy)ethyl trimethylammonium chloride (2-(methacryloyloxy)ethyl trimethylaminium chloride), 2-(acryloyloxy)ethyl trimethylammonium chloride (2-(acryloyloxy)ethyl trimethylaminium chloride), 2-(methacryloyloxy)ethyl dimethylammonium chloride (2-(methacryloyloxy)ethyl dimethylethylaminium chloride), and 2-(acryloyloxy)ethyl dimethylethylammonium chloride (2-(acryloyloxy)ethyl dimethylethylaminium chloride).

The radical polymerization of a hydrophilic monomer in the step 2 is carried out, for example, as follows: a solution of an alkali metal salt and a hydrophilic monomer is applied (sprayed) onto the surface of the object on which a benzophenone or thioxanthone compound or the like has been adsorbed, or alternatively, the object is immersed in a solution of an alkali metal salt and a hydrophilic monomer; and then the object is irradiated with UV light to allow radical polymerization (photoradical polymerization) of the monomer to proceed, whereby polymer chains are grown on the surface of the object. After the application, the surface may further be covered with a transparent cover of glass, PET, polycarbonate or other materials, followed by irradiation with UV light through the transparent cover to allow radical polymerization (photoradical polymerization) of the monomer to proceed, whereby polymer chains are grown on the surface of the object.

The solvent for application (spraying), the method for application (spraying), the method for immersion, the conditions for irradiation, and other conditions may be conventionally known materials or methods. The solution of the radically polymerizable monomer may be an aqueous solution, or a solution in an organic solvent that does not dissolve the photopolymerization initiator used (e.g. a benzophenone or thioxanthone compound). Moreover, the solution of the radically polymerizable monomer may contain a known polymerization inhibitor such as 4-methylphenol.

In the present invention, the radical polymerization of the hydrophilic monomer is allowed to proceed by light irradiation after the application of the hydrophilic monomer solution or after the immersion in the hydrophilic monomer solution. In the light irradiation, UV light sources with an emission wavelength mainly in the ultraviolet region, such as high-pressure mercury lamps, metal halide lamps, and LED lamps, can be suitably used. The light dose may be selected appropriately in view of polymerization time and uniform progress of the reaction. Moreover, in order to prevent inhibition of polymerization due to active gas such as oxygen in the reaction vessel and the reaction pipe, oxygen is preferably removed from the reaction vessel, the reaction pipe, and the reaction solution during or before the light irradiation. To this end, appropriate operations may be performed; for example, an inert gas such as nitrogen gas or argon gas is introduced into the reaction vessel, the reaction pipe, and the reaction solution to discharge active gas such as oxygen from the reaction system and replace the atmosphere in the reaction system with the inert gas. Furthermore, in order to prevent inhibition of the reaction due to oxygen and the like, for example, a measure may also appropriately be taken in which an UV light source is placed such that an air layer (oxygen content: 15% or higher) does not exist between the reaction vessel made of glass, plastic or the like and the reaction solution or the object intended to be modified.

The ultraviolet light used has a wavelength of 300 to 400 nm. Such a wavelength enables polymer chains to be formed well on the surface of the object. Examples of light sources that can be used include high-pressure mercury lamps, LEDs with a center wavelength of 365 nm, LEDs with a center wavelength of 375 nm, and LEDs with a center wavelength of 385 nm. More preferred is irradiation with LED light having a wavelength of 355 to 390 nm. In particular, for example, LEDs with a center wavelength of 365 nm, which is close to the excitation wavelength (366 nm) of benzophenone, are preferred in view of efficiency. Light having a wavelength of less than 300 nm can cleave and damage molecules of the object intended to be modified. For this reason, light having a wavelength of 300 nm or greater is preferred. More preferred is light having a wavelength of 355 nm or greater because it produces very little damage to the object intended to be modified. In contrast, light having a wavelength of greater than 400 nm is less likely to activate the photopolymerization initiator, so that the polymerization reaction does not readily proceed. For this reason, light having a wavelength of 400 nm or less is preferred. Although LED light is suitable because the wavelength range of LED light is narrow so that no wavelengths other than the center wavelength are emitted, a mercury lamp or the like can also achieve similar effects to those of LED light if a filter is used to block light with wavelengths less than 300 nm.

In the present invention, polymer chains can be produced with good productivity by reducing the duration of irradiation with light having a wavelength of 300 to 400 nm. For example, the duration of light irradiation may be 3 to 120 minutes, and can also be reduced to 5 to 100 minutes, or 10 to 60 minutes.

Another aspect of the present invention is a method for surface-modifying an object made of a rubber vulcanizate or a thermoplastic resin, which includes a step I of radically polymerizing a hydrophilic monomer by irradiation with UV light having a wavelength of 300 to 400 nm in the presence of a photopolymerization initiator and an alkali metal salt to grow polymer chains on the surface of the object. Specifically, a hydrophilic monomer is radically polymerized by irradiation with UV light in the presence of a photopolymerization initiator used as the initiator and, further, an alkali metal salt to form hydrophilic polymer chains, whereby a surface-modified body can be produced in which a hydrophilic polymer layer (hydrophilic polymer) is fixed to the surface of an object intended to be modified. The object to be modified, the photopolymerization initiator, the alkali metal salt, and the hydrophilic monomer used in the step I may be as described hereinabove.

Preferably, the step of making the surface hydrophilic as described above is performed before the step I. Similarly to the above, the surface that has been made hydrophilic by the step has better compatibility with an organic solvent containing the photopolymerization initiator dissolved therein, with the result that a greater amount of the photopolymerization initiator is more uniformly adsorbed on the surface of the object in the step I.

For example, the step I may be carried out by contacting the surface of the object with a photopolymerization initiator, an alkali metal salt, and a hydrophilic monomer, and then irradiating the surface with LED light having a wavelength of 300 to 400 nm to form polymerization initiation points from the photopolymerization initiator while radically polymerizing the hydrophilic monomer starting from the polymerization initiation points in the presence of the alkali metal salt to grow polymer chains.

The radical polymerization of a hydrophilic monomer in the step I may be carried out as follows: a solution of a hydrophilic monomer containing a photopolymerization initiator such as a benzophenone or thioxanthone compound and an alkali metal salt is applied (sprayed) onto the surface of the object to be modified, or alternatively, the object to be modified is immersed in a solution of a hydrophilic monomer containing a photopolymerization initiator and an alkali metal salt; and then the object is irradiated with UV light to allow radical polymerization (photoradical polymerization) of the monomer to proceed, whereby polymer chains are grown on the surface of the object. Further, the surface may be covered with a transparent cover of glass, PET, polycarbonate or other materials, followed by irradiation with UV light through the transparent cover as described hereinabove. The solvent for application (spraying), the method for application (spraying), the method for immersion, the conditions for irradiation, and other conditions may be the materials or methods described hereinabove. Moreover, similarly to the above, the duration of irradiation with light having a wavelength of 300 to 400 nm may be reduced to 3 to 120 minutes, 5 to 100 minutes, or 10 to 60 minutes.

In the step 2 or step I, two or more types of monomers may be radically polymerized simultaneously. Moreover, multiple types of polymer chains may be grown on the surface of the object. In the surface modification methods of the present invention, the polymer chains may be cross-linked to one another. In this case, the polymer chains may be cross-linked to one another by ionic crosslinking, cross-linking by a hydrophilic group containing an oxygen atom, or crosslinking by a halogen group such as iodine.

The surface modification methods can be applied to rubber vulcanizates or thermoplastic resins to produce surface-modified bodies. Moreover, the methods may be applied to at least a part of the surface of three-dimensional solid bodies to produce surface-modified bodies with modified properties. Furthermore, preferred examples of such surface-modified bodies include polymer brushes. The term "polymer brush" means an assembly of graft polymer molecules obtained in the "grafting from" approach by surface-initiated polymerization. Moreover, the graft chains are preferably oriented in a direction substantially vertical to the surface of the modified object because then the entropy decreases to reduce the molecular mobility of the graft chains, thereby providing lubricity. Furthermore, semidilute or concentrated brushes having a brush density of 0.01 chains/nm$^2$ or higher are preferred.

The surface modification methods may also be applied to rubber vulcanizates or thermoplastic resins to produce medical devices such as matrices, filters, channels, or tubes for medical and healthcare use, at least part of whose surface is modified. The modification may preferably be applied to at least a surface portion to be in contact with blood or biological fluids of a medical device such as a matrix (e.g. a matrix for collecting and adsorbing a specific protein or specific cells, such as cancer cells, from a blood sample or a biological fluid sample), filter, channel, or tube for medical and healthcare use. The entire surface may be modified. By appropriately selecting the type of hydrophilic monomer according to the desired properties, proteins and cells in blood or biological fluids can be prevented from adhering or adsorbing to the surface, or the surface can selectively adhere or adsorb to cancer cells or other cells, and it is also possible to obtain excellent durability because the polymer chains are fixed.

EXAMPLES

The present invention is described below in more detail with reference to examples, but the present invention is not limited thereto.

Example 1

A 3 wt % solution of benzophenone in acetone was applied to the surface of a polyethylene terephthalate (PET)

object intended to be modified, so that benzophenone was adsorbed to the surface, followed by drying. Then, the surface was irradiated with LED light (5 mW/cm$^2$) having a wavelength of 365 nm for 60 minutes while the object was rotated so that the entire surface was irradiated with light.

Subsequently, the surface was immersed in an aqueous solution of acrylamide (1.25 M) containing sodium chloride adjusted at a concentration of 1.5 M in a glass reaction vessel. The reaction vessel was sealed with a rubber stopper, and argon gas was introduced and allowed to bubble through the solution for 120 minutes to remove oxygen. While being rotated, the glass reaction vessel was irradiated with LED light having a wavelength of 365 nm for 30 minutes to cause radical polymerization, whereby polymer chains were grown on the PET surface. Thus, a surface-modified body (polymer brush) was prepared.

Example 2

A 3 wt % solution of benzophenone in acetone was applied to the surface of a PET object intended to be modified, so that benzophenone was adsorbed to the surface, followed by drying.

Subsequently, the surface was immersed in an aqueous solution of acrylamide (1.25 M) containing sodium chloride adjusted at a concentration of 1.5 M in a glass reaction vessel. The reaction vessel was sealed with a rubber stopper, and argon gas was introduced and allowed to bubble through the solution for 120 minutes to remove oxygen. While being rotated, the glass reaction vessel was irradiated with LED light having a wavelength of 365 nm for 30 minutes to cause radical polymerization, whereby polymer chains were grown on the PET surface. Thus, a surface-modified body (polymer brush) was prepared.

Example 3

Water containing 0.015 wt % benzophenone dissolved therein was used to prepare an aqueous solution containing acrylamide and sodium chloride adjusted at concentrations of 1.25 M and 1.5 M, respectively. The surface of a PET object to be modified was immersed in the aqueous solution in a glass reaction vessel. The glass reaction vessel was sealed with a rubber stopper, and argon gas was introduced and allowed to bubble through the solution for 120 minutes to remove oxygen. While being rotated, the glass reaction vessel was irradiated with LED light having a wavelength of 365 nm for 30 minutes to cause radical polymerization, whereby polymer chains were grown on the PET surface. Thus, a surface-modified body (polymer brush) was prepared.

Example 4

A surface-modified body (polymer brush) was prepared in the same manner as in Example 1, except that potassium chloride (0.75 M) was used instead of sodium chloride (1.5 M) and the irradiation time was 60 minutes.

Example 5

A surface-modified body (polymer brush) was prepared in the same manner as in Example 2, except that 2-methoxyethyl acrylate was used instead of acrylamide.

Example 6

A surface-modified body (polymer brush) was prepared in the same manner as in Example 3, except that 2-methoxyethyl acrylate was used instead of acrylamide.

Example 7

A surface-modified body (polymer brush) was prepared in the same manner as in Example 4, except that 2-methoxyethyl acrylate was used instead of acrylamide.

Example 8

A surface-modified body (polymer brush) was prepared in the same manner as in Example 2, except that 2-methacryloyloxyethyl phosphorylcholine was used instead of acrylamide.

Example 9

A surface-modified body (polymer brush) was prepared in the same manner as in Example 2, except that 2-(methacryloyloxy)ethyl trimethylammonium chloride was used instead of acrylamide.

Example 10

A surface-modified body (polymer brush) was prepared in the same manner as in Example 2, except that potassium 3-sulfopropyl methacrylate was used instead of acrylamide.

Example 11

A 3 wt % solution of benzophenone in acetone was applied to the surface of a PET object intended to be modified, so that benzophenone was adsorbed to the surface, followed by drying.

Subsequently, an aqueous solution of 2-methoxyethyl acrylate (1.25 M) containing sodium chloride adjusted at a concentration of 1.5 M was applied to the surface of the object, and the surface was covered with glass.

Then, the object was irradiated through the glass with LED light having a wavelength of 365 nm for 30 minutes to cause radical polymerization, whereby polymer chains were grown on the PET surface. Thus, a surface-modified body (polymer brush) was prepared.

Example 12

A surface-modified body (polymer brush) was prepared in the same manner as in Example 5, except that a polystyrene (PS) was used instead of the PET.

Example 13

A surface-modified body (polymer brush) was prepared in the same manner as in Example 5, except that an acrylic resin was used instead of the PET.

Example 14

A surface-modified body (polymer brush) was prepared in the same manner as in Example 5, except that the surface was made hydrophilic by irradiation for 5 minutes using a low-pressure mercury lamp (having spectrum peaks at 185 nm and 254 nm) before benzophenone was adsorbed to the PET.

Example 15

A surface-modified body (polymer brush) was prepared in the same manner as in Example 6, except that the surface was made hydrophilic by irradiation for 5 minutes using a low-pressure mercury lamp (having spectrum peaks at 185 nm and 254 nm) before benzophenone was adsorbed to the PET.

Comparative Example 1

An untreated PET was used.

Comparative Example 2

A 3 wt % solution of benzophenone in acetone was applied to the surface of a polyethylene terephthalate (PET) object intended to be modified, so that benzophenone was adsorbed to the surface, followed by drying. Subsequently, the surface was irradiated with LED light (5 mW/cm$^2$) having a wavelength of 365 nm for 60 minutes. During the irradiation, the object was rotated so that the entire surface was irradiated with light.

Subsequently, the surface was immersed in an aqueous solution of acrylamide (1.25 M) in a glass reaction vessel. The glass reaction vessel was sealed with a rubber stopper, and argon gas was introduced and allowed to bubble through the solution for 120 minutes to remove oxygen. While being rotated, the glass reaction vessel was irradiated with LED light having a wavelength of 365 nm for 300 minutes to cause radical polymerization, whereby polymer chains were grown on the PET surface. Thus, a surface-modified body (polymer brush) was prepared.

The surface-modified bodies prepared in the examples and the comparative examples were evaluated as follows.
(Protein Adsorption)

The surface of the sample (surface-modified body) was brought into contact with a 1 mg/ml solution of bovine serum albumin (BSA), followed by standing at 37° C. for 3 hours. The surface of the sample was lightly washed with phosphate buffered saline to prepare a protein adsorbed sample. The whole amount of the protein adsorbed sample was put into a 50-ml centrifuge tube, and the proteins adsorbed on the surface of the sample were extracted in accordance with the method described in Section 3.6, Water-soluble proteins, in JIS T9010: 1999, "Test methods relevant to biological safety of rubber products." To the extracted proteins was accurately added 0.5 ml of a 0.1 mol/l aqueous solution of sodium hydroxide, and the proteins were dissolved to prepare a sample solution. Separately, a blank was prepared by following the same procedure, but without adding the sample.

A volume of 0.2 ml each of the sample solution and reference solutions (5-100 μg/ml BSA solutions) were accurately weighed and assayed for protein amount by the Lowry method. A calibration curve was prepared using the BSA concentration (μg/ml) and the absorbance of each reference solution, and the protein concentration (μg/ml) per milliliter of the sample solution was calculated from the calibration curve and converted to a value per area of the surface-modified body.

(Protein Adsorption after Durability Testing)

After a protein adsorption test was performed, the surface was immersed and washed in hot water at 70° C. to wash away proteins. The adsorption and washing operations were repeated 10 times, and then a protein adsorption test was performed again to determine the amount of protein adsorption after durability testing and the rate of increase from the initial amount of protein adsorption.

TABLE 1

|  | Example | | | | | | | | |
| --- | --- | --- | --- | --- | --- | --- | --- | --- | --- |
|  | 1 | 2 | 3 | 4 | 5 | 6 | 7 | 8 | 9 |
| Protein adsorption (μg/cm$^2$) | 0.31 | 0.30 | 0.32 | 0.32 | 0.15 | 0.16 | 0.17 | 0.11 | 0.45 |
| Protein adsorption after durability testing (μg/cm$^2$) | 0.32 | 0.31 | 0.33 | 0.33 | 0.16 | 0.17 | 0.18 | 0.12 | 0.47 |
| Rate of increase | 3.1% | 3.2% | 3.0% | 3.0% | 6.3% | 5.9% | 5.8% | 8.3% | 4.3% |

TABLE 2

|  | Example | | | | | | Comparative Example | |
| --- | --- | --- | --- | --- | --- | --- | --- | --- |
|  | 10 | 11 | 12 | 13 | 14 | 15 | 1 | 2 |
| Protein adsorption (μg/cm$^2$) | 0.12 | 0.31 | 0.31 | 0.30 | 0.15 | 0.155 | 1.89 | 0.32 |
| Protein adsorption after durability testing (μg/cm$^2$) | 0.13 | 0.32 | 0.32 | 0.31 | 0.155 | 0.16 | 2.25 | 0.33 |
| Rate of increase | 7.7% | 3.1% | 3.1% | 3.2% | 3.2% | 3.1% | 19% | 3.0% |

According to the results in Tables 1 and 2, the surface-modified bodies of the examples each exhibited a low protein adsorption, and also had a low rate of increase in protein adsorption after repeated adsorption and washing. In contrast, the untreated PET surface in Comparative Example 1 even initially exhibited a high adsorption, and also had a high rate of increase in protein adsorption after repeated adsorption and washing. It should be noted that since cells adhere or adsorb to the surface via proteins adsorbed thereon, a lower protein adsorption indicates that cells are also less likely to adhere or adsorb to the surface. Moreover, comparison between Comparative Example 2 and Example 1 shows that comparable or better properties were achieved by addition of an alkali metal salt even with a greatly reduced irradiation time, which is very economical.

It is clear from these results that it is possible to reduce protein adsorption and cell adsorption and at the same time to provide durability after repeated use by forming polymer chains on the surface of medical devices such as matrices, filters, channels, or tubes for medical and healthcare use from a hydrophilic monomer such as acrylamide, 2-methoxyethyl acrylate, or 2-methacryloyloxyethyl phosphorylcholine in the presence of an alkali metal salt.

Furthermore, the 2-methoxyethyl acrylate polymer grown in Examples 5 to 7 is a material that does not adsorb platelets, white blood cells, and red blood cells in blood, but selectively adsorbs only cancer cells. Such a polymer is expected to be used, for example, to selectively adhere or adsorb only cancer cells in blood containing cancer cells.

The invention claimed is:

1. A method for suppressing adsorption of proteins or cells to an object made of a rubber vulcanizate or a thermoplastic resin, the method comprising:
   a step 1 of forming polymerization initiation points on a surface of the object; and
   a step 2 of radically polymerizing a hydrophilic monomer starting from the polymerization initiation points by irradiation with UV light having a wavelength of 300 to 400 nm for 3 minutes or more in the presence of an alkali metal salt so as to grow polymer chains on the surface of the object,
   wherein the alkali metal salt is at least one selected from the group consisting of halogenated alkali metal salts, alkali metal carbonates, alkali metal bicarbonates, alkali metal hydrogen carbonates, alkali metal nitrates, alkali metal sulfates, alkali metal bisulfates, alkali metal phosphates, alkali metal hydroxides, alkali metal acetates, alkali metal citrates, and alkali metal lactates; and
   wherein the alkali metal salt is a water-soluble lithium, sodium, potassium, rubidium or cesium salt.

2. A method for suppressing adsorption of proteins or cells to an object made of a rubber vulcanizate or a thermoplastic resin, the method comprising
   a step I of radically polymerizing a hydrophilic monomer by irradiation with UV light having a wavelength of 300 to 400 nm for 3 minutes or more in the presence of a photopolymerization initiator and an alkali metal salt so as to grow polymer chains on a surface of the object, wherein
   the alkali metal salt is at least one selected from the group consisting of halogenated alkali metal salts, alkali metal carbonates, alkali metal bicarbonates, alkali metal hydrogen carbonates, alkali metal nitrates, alkali metal sulfates, alkali metal bisulfates, alkali metal phosphates, alkali metal hydroxides, alkali metal acetates, alkali metal citrates, and alkali metal lactates;
   the alkali metal salt is a water-soluble lithium, potassium, rubidium or cesium salt
   the photopolymerization initiator is at least one selected from the group consisting of
   (i) a benzophenone compound represented by the following formula:

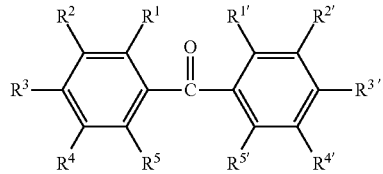

wherein $R^1$ to $R^5$ and $R^{1'}$ to $R^{5'}$ are the same as or different from one another and each represent a hydrogen atom, an alkyl group, a halogen, a hydroxy group, a primary to tertiary amino group, a mercapto group, or a hydrocarbon group optionally containing an oxygen, nitrogen, or sulfur atom, and any two adjacent groups of $R^1$ to $R^3$ and $R^{1'}$ to $R^{5'}$ may be joined together to form a ring with the carbon atoms to which they are attached; and
   (ii) a thioxanthone compound represented by the following formula:

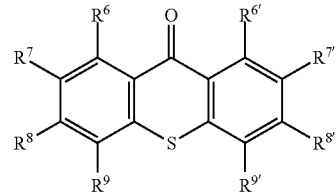

wherein $R^6$ to $R^9$ and $R^{6'}$ to $R^{9'}$ are the same as or different from one another and each represent a hydrogen atom, a halogen atom, or an alkyl, cyclic alkyl, aryl, alkenyl, alkoxy, or aryloxy group.

3. The method according to claim 1, wherein step 1 comprises adsorbing a photopolymerization initiator to a surface of the object, optionally followed by irradiation with UV light having a wavelength of 300 to 400 nm, to form polymerization initiation points from the photopolymerization initiator on the surface.

4. The method according to claim 1, wherein before step 1 is conducted, a preliminary step is conducted whereby the surface of the object is made hydrophilic by irradiation with light having a wavelength of 160 to 300 nm.

5. The method according to claim 3, wherein the photopolymerization initiator is at least one of a benzophenone compound or a thioxanthone compound.

6. The method according to claim 1, wherein the alkali metal salt is at least one of sodium chloride or potassium chloride.

7. The method according to claim 1, wherein during or before the light irradiation in step 1, an inert gas is introduced into a reaction vessel, a reaction pipe, and a reaction solution so that the monomer is polymerized in an atmosphere replaced with the inert gas.

8. The method according to claim 1, wherein the radical polymerization of the hydrophilic monomer in the step 2 is carried out by applying or spraying a solution of the hydrophilic monomer onto the surface of the object, and then covering the applied or sprayed object with a transparent cover of glass or resin, followed by irradiation with the UV light through the transparent cover of glass or resin to radically polymerize the monomer.

9. The method according to claim 1, wherein the hydrophilic monomer is at least one selected from the group consisting of acrylic acid, acrylic acid esters, alkali metal salts of acrylic acid, amine salts of acrylic acid, methacrylic acid, methacrylic acid esters, alkali metal salts of methacrylic acid, amine salts of methacrylic acid, acrylonitrile, acrylamide, dimethylacrylamide, diethylacrylamide, isopropylacrylamide, hydroxyethylacrylamide, methoxyethylacrylamide, acryloylmorpholine, methacrylamide, dimethylmethacrylamide, diethylmethacrylamide, isopropylmethacrylamide, hydroxyethylmethacrylamide, methoxyethylmethacrylamide, and methacryloylmorpholine.

10. The method according to claim 1, wherein the hydrophilic monomer is an alkali metal salt-containing monomer.

11. The method according to claim 10, wherein the alkali metal salt-containing monomer is at least one selected from the group consisting of alkali metal salts of acrylic acid, methacrylic acid, itaconic acid, 3-vinylpropionic acid, vinylsulfonic acid, 2-sulfoethyl (meth)acrylate, 3-sulfopropyl (meth)acrylate, 2-acrylamide-2-methylpropanesulfonic acid, or styrenesulfonic acid.

12. The method according to claim 1, wherein the hydrophilic monomer is a halogen-containing monomer.

13. The method according to claim 12, wherein the halogen-containing monomer is a nitrogen-containing monomer.

14. The method according to claim 13, wherein the nitrogen-containing monomer is at least one of 2-(methacryloyloxy)ethyl trimethylammonium chloride or 2-(acryloyloxy)ethyl trimethylammonium chloride.

15. The method according to claim 1, wherein the hydrophilic monomer is a zwitterionic monomer.

16. The method according to claim 8, wherein the solution of the hydrophilic monomer contains a polymerization inhibitor, and the monomer is polymerized in the presence of the polymerization inhibitor.

17. A surface-modified body, produced by the method according to claim 1.

18. A surface-modified body, produced by the method according to claim 1, to which proteins and cells in blood or biological fluids are less likely to adhere or adsorb.

19. A surface-modified body, produced by the method according to claim 1, to which a specific protein or specific cells in blood or biological fluids are more likely to selectively adhere or adsorb.

20. A surface-modified body, comprising a three-dimensional solid body at least part of whose surface is modified by the method according to claim 1.

21. A matrix for medical and healthcare use, at least part of whose surface is modified by the method according to claim 1.

22. A filter for medical and healthcare use, at least part of whose surface is modified by the method according to claim 1.

23. A channel for medical and healthcare use, at least part of whose surface is modified by the method according to claim 1.

24. A tube for medical and healthcare use, at least part of whose surface is modified by the method according to claim 1.

* * * * *